(12) United States Patent
Buehler et al.

(10) Patent No.: US 11,363,833 B2
(45) Date of Patent: Jun. 21, 2022

(54) BLISTER CAPSULE, AND CONTAINER, FOR AN AEROSOL-GENERATING SYSTEM

(71) Applicant: Philip Morris Products S.A., Neuchatel (CH)

(72) Inventors: Frederic Ulysse Buehler, Neuchatel (CH); Rui Nuno Batista, Morges (CH)

(73) Assignee: Philip Morris Products S.A., Neuchatel (CH)

( * ) Notice: Subject to any disclaimer, the term of this patent is extended or adjusted under 35 U.S.C. 154(b) by 2 days.

(21) Appl. No.: 15/738,155

(22) PCT Filed: Aug. 8, 2016

(86) PCT No.: PCT/EP2016/068906
§ 371 (c)(1),
(2) Date: Dec. 20, 2017

(87) PCT Pub. No.: WO2017/029149
PCT Pub. Date: Feb. 23, 2017

(65) Prior Publication Data
US 2018/0177223 A1    Jun. 28, 2018

(30) Foreign Application Priority Data

Aug. 14, 2015 (EP) ..................................... 15181164

(51) Int. Cl.
*A24B 15/167* (2020.01)
*B65D 75/32* (2006.01)
(Continued)

(52) U.S. Cl.
CPC ............ *A24B 15/167* (2016.11); *A24F 40/30* (2020.01); *A24F 40/42* (2020.01); *B65D 75/324* (2013.01);
(Continued)

(58) Field of Classification Search
CPC ....... A24B 15/167; A24D 1/14; A24F 47/002; A24F 40/42; A24F 40/30; A24F 40/10;
(Continued)

(56) References Cited

U.S. PATENT DOCUMENTS 4,544,592 A * 10/1985 Spector ..................... A61L 9/03
239/56
4,865,056 A * 9/1989 Tamaoki ................ A24D 3/061
131/337

(Continued)

FOREIGN PATENT DOCUMENTS

CN    1369415 A    9/2002
CN    1882314 A    12/2006
(Continued)

OTHER PUBLICATIONS

Extended European Search Report dated Nov. 4, 2019 in Patent Application No. 19186168.1, 7 pages.
(Continued)

Primary Examiner — Darren W Gorman
Assistant Examiner — Juan C Barrera
(74) Attorney, Agent, or Firm — Oblon, McClelland, Maier & Neustadt, L.L.P.

(57) ABSTRACT

A blister capsule for an aerosol-generating system, and a container including blister capsules, are provided, the blister capsule including a blister shell; a tubular porous element disposed in the blister shell; a volatile liquid sorbed on the tubular porous element; and a film configured to seal the blister shell, the film and the blister shell being frangible, and the container including at least two of the blister capsules coupled together by a hollow tubular canister configured as a mixing chamber for the volatile liquids contained in each of the blister capsules.

**7 Claims, 5

(51) Int. Cl.
*A24F 40/30* (2020.01)
*A24F 40/42* (2020.01)
*A24F 40/10* (2020.01)

(52) U.S. Cl.
CPC ............ B65D 75/326 (2013.01); *A24F 40/10* (2020.01); *A61L 2209/133* (2013.01)

(58) Field of Classification Search
CPC ............... B65D 75/324; B65D 75/326; A61L 2209/131; A61L 2209/133; A61L 9/125; A61L 9/035; A61L 9/03; A61L 9/04; A01M 1/2044; A01M 1/2055
USPC ............ 239/47, 51.5, 53, 54, 55, 56, 57, 34; 206/85–96
See application file for complete search history.

(56) References Cited

U.S. PATENT DOCUMENTS

| | | | | |
|---|---|---|---|---|
| 7,846,485 | B2* | 12/2010 | Blanc | B65D 85/8061 426/77 |
| 2008/0099576 | A1* | 5/2008 | Hart | A61L 9/12 239/53 |
| 2008/0185011 | A1 | 8/2008 | Sherwood | |
| 2010/0018523 | A1 | 1/2010 | Staniforth et al. | |
| 2010/0178042 | A1* | 7/2010 | Neumann | A01M 1/2077 392/386 |
| 2013/0146489 | A1 | 6/2013 | Scatterday | |
| 2013/0168270 | A1 | 7/2013 | Koizumi et al. | |
| 2014/0076989 | A1* | 3/2014 | Granger | A61L 9/12 239/52 |
| 2014/0202478 | A1* | 7/2014 | Awty | A24D 3/061 131/332 |
| 2014/0209111 | A1 | 7/2014 | Russell et al. | |
| 2015/0108239 | A1* | 4/2015 | Bourne | B60H 3/0028 239/6 |
| 2015/0291337 | A1 | 10/2015 | Koizumi et al. | |
| 2016/0331913 | A1* | 11/2016 | Bourque | A61M 11/042 |

FOREIGN PATENT DOCUMENTS

| | | | | |
|---|---|---|---|---|
| CN | | 101070111 A | 11/2007 | |
| CN | | 101548152 A | 9/2009 | |
| CN | | 101842221 A | 9/2010 | |
| CN | | 102482019 A | 5/2012 | |
| CN | | 102849336 A | 1/2013 | |
| CN | | 103826988 A | 5/2014 | |
| CN | | 104443486 A | 3/2015 | |
| CN | | 104822281 A | 8/2015 | |
| EP | | 2 612 824 A1 | 7/2013 | |
| EP | | 2 706 877 A1 | 3/2014 | |
| EP | | 2 745 717 A1 | 6/2014 | |
| JP | | 2014-525237 A | 9/2014 | |
| KZ | | 28017 B | 12/2013 | |
| RU | | 2 336 002 C2 | 10/2008 | |
| WO | | 2007/090594 A1 | 8/2007 | |
| WO | | 2012/029323 A1 | 3/2012 | |
| WO | | 2012/156708 A1 | 11/2012 | |
| WO | WO 2014/140087 A1 | | 9/2014 | |
| WO | | 2014/159982 A1 | 10/2014 | |
| WO | WO 2015/040180 A2 | | 3/2015 | |
| WO | | 2015/101479 A1 | 7/2015 | |
| WO | WO2015116934 | * | 8/2015 | ............ A61M 11/04 |
| WO | WO 2015/197502 A1 | | 12/2015 | |
| WO | WO 2016/135224 A1 | | 9/2016 | |
| WO | WO 2016/156212 A1 | | 10/2016 | |

OTHER PUBLICATIONS

Russian Decision to Grant dated Sep. 26, 2019, in Patent Applicatio No. 2017144175, 16 pages (with English translation).
International Search Report and Written Opinion dated Dec. 23, 2016 in PCT/EP2016/068906, filed Aug. 8, 2016.
Office Action and Search Report dated Apr. 26, 2020 in corresponding Chinese Patent Application No. 201680042232.0, along with an English translation.
Decision to Grant a Patent dated Sep. 23, 2020 in Japanese Application No. 2018-503640, along with an English translation.

* cited by examiner

BLISTER CAPSULE, AND CONTAINER, FOR AN AEROSOL-GENERATING SYSTEM

The present invention relates to a blister capsule for an aerosol-generating system, and to a container comprising blister capsules. In particular, the invention relates to a blister capsule comprising a porous element having a volatile liquid sorbed thereon.

Aerosol-generating devices often comprise a closed container with one or more aerosol-generating agents like for example a flavourant like menthol or a nicotine containing substrate. These known systems may generate an aerosol by heating, but not combusting, solid or liquid aerosol-generating substrate. In order to store and release the aerosol-generating agent, the container needs to be sealed, but easily broken or pierced.

It is an object of the present invention to provide an improved container for aerosol-generating systems that is preferably easy to manufacture, cost effective in production, and enables more accurate control of the volume of liquid stored and delivered. It is also an object of the present invention to provide an improved container for containing multiple types of aerosol-generating agents that is also preferably easy to manufacture, cost effective in production, and enables more accurate control of the volume of liquid stored and delivered.

According to a first aspect of the present invention, there is provided a blister capsule for an aerosol-generating system. The blister capsule comprises: a blister shell; a tubular porous element disposed in the blister shell; a volatile liquid sorbed on the tubular porous element; and a film configured to seal the blister shell. The film and the blister shell are frangible.

By providing such a blister capsule, a stable container for volatile liquid is provided, which may be manufactured easily, cost effectively, and at high volume, using standard manufacturing processes. In addition, the blister capsule of the present invention may enable a controlled volume of volatile liquid to be sorbed on a porous element for use in an aerosol-generating system.

The sealing film may be may be peeled away just prior to use, or pierced, ruptured or otherwise broken, to open the capsule and release the volatile liquid.

The film for sealing the blister shell is preferably planar. The film for sealing the blister shell may not be planar, which may enable the volume of the sealed blister capsule to be increased.

A longitudinal axis of the tubular porous element may by aligned with a longitudinal axis of the blister shell. The shape outer dimensions of the cross-section perpendicular to the longitudinal axis of the tubular porous element may be substantially equal to the inner shape and dimensions of the cross-section perpendicular to the longitudinal axis of the blister shell. In this way, the tubular porous element may be retained in position in the blister shell more easily.

The porous element is provided as a tubular element. This may enable an airflow pathway to be formed when the blister capsule is opened, pierced or otherwise ruptured. For example, the tubular element enables a piercing element to pierce both the blister shell and the sealing film without affecting the tubular porous element.

The tubular porous element may be made from any suitable absorbent plug or body, for example, a foamed metal or plastics material, polypropylene, terylene, nylon fibres or ceramic.

The blister shell preferably comprises a cavity and a flange extending around the periphery of the cavity. The tubular porous element is disposed in the cavity of the blister shell. The film is preferably sealed to the flange. The film may be sealed to the blister shell of the capsule using any suitable method, including: adhesive, such as an epoxy adhesive; heat sealing; ultrasonic welding; and laser welding.

The blister capsule preferably has a substantially circular cross-section. A circular cross-section is particularly advantageous for reducing manufacturing complexity. However, any suitable cross-sectional shape may be used depending on the requirements of the capsule. For example, the cross-sectional shape may be triangular, rectangular, or elliptical.

The blister capsule is preferably thin, that is to say, the depth of the blister shell is preferably less than the diameter of the blister shell.

The blister shell preferably has an internal diameter of between about 3 mm and about 15 mm, more preferably about 5 mm and about 10 mm.

The blister shell preferably has a depth, that is to say a longitudinal length, of between about 2 mm and about 12 mm, more preferably between about 3 mm and about 8 mm.

The tubular porous portion preferably has a longitudinal length substantially equal to the depth of the blister shell.

Preferably, the blister capsule is configured to hold between about 5 microlitres and about 50 microlitres of volatile liquid, more preferably between about 10 microlitres and about 30 microlitres of volatile liquid.

The blister capsule may further comprise a further blister shell comprising a volatile liquid. The film is preferably further configured to seal the further blister shell. A further tubular porous element may be disposed in the further blister shell. Each blister shell may comprise a different volatile liquid. In embodiments comprising a blister shell and a further blister shell, the blister shell will be referred to as a first blister shell and the further blister shell will be referred to as a second blister shell.

The volume of the first blister shell and the volume of the second blister shell may be the same or different. In one embodiment, the volume of the second blister shell is greater than the volume of the first blister shell.

The blister shell is preferably formed from a laminate material comprising at least two layers. Each layer may be formed from a metal film, preferably aluminium more preferably food grade, anodised aluminium, or a polymer such as polypropylene, polyurethane, polyethylene, fluorinated ethylene propylene. At least one layer of the laminate material may be paper or cardboard. The layers of the laminate may be bonded together using adhesive, heat, or pressure. When the laminate comprises a layer of aluminium and a layer of polymer material, the polymer material may be a coating. The coating layer may be thinner than the aluminium layer. The polymer layer material, and thickness, is preferably chosen in dependence on the composition of the volatile liquid to be contained. For example, the polymer layer is preferably chosen to reduce oxidation, and or reaction with the container, of the contained liquid. The laminate material may comprise more than two layers.

According to a second aspect of the present invention, there is provided a container for an aerosol-generating system. The container comprises: a plurality of blister capsules each capsule comprising: a blister shell; a volatile liquid disposed in the blister shell; and a film configured to seal the blister shell. The film and the blister shell are frangible. The container further comprises a hollow tubular canister comprising: a first end; a second end; and a mixing chamber disposed between the first end and the second end. At least one blister capsule is coupled to the first end of the hollow tubular canister and at least one blister capsule is coupled to the second end of the hollow tubular canister.

Advantageously, providing a container for an aerosol-generating system having blister capsules and a mixing chamber enables the container to be manufactured more easily, while providing an easy to use container that enables the mixing of aerosol components.

Each of the first end and the second end of the hollow tubular canister preferably comprises a lip configured to engage with a respective one of the blister capsules. The dimensions of the orifice formed by the lip are preferably substantially equal to the external dimensions of the cross-section of the blister shell. The blister capsules may be a press-fit within the orifices.

The free edge of the lip may extend away from a longitudinal axis of the hollow tubular canister. Alternatively, the free edge of the lip may extend towards a longitudinal axis of the hollow tubular canister. The lip preferably forms a surface, the blister capsule abutting the surface to form a sealed container. The blister capsule may be coupled to the lip of the canister by an adhesive, such as an epoxy-resin, or by heat sealing, ultrasonic welding or laser welding.

The cross-section perpendicular to the longitudinal axis of the canister is preferably circular. However, any suitable cross-sectional shape may be used depending on the requirements of the capsule. For example, the cross-sectional shape may be triangular, rectangular, or elliptical.

The outer diameter of the canister may be substantially equal to the outer diameter of the blister capsule. Where the blister capsule comprises a flange, the outer diameter of the canister is preferably substantially equal to the outer diameter of the flange.

One or more of the blister capsules of the container according to the second aspect of the invention may be a blister capsule according to the first aspect of the invention.

The blister shell coupled to the canister may comprise a tubular porous element for sorbing the volatile liquid, as described above. As will be appreciated, the container according to the present invention may comprise a plurality of the blister capsules as described herein. The blister capsules may be the same, and may comprise the same or different volatile liquids. The blister capsules may be different, and may comprise the same or different volatile liquids.

The hollow tubular canister may comprise a tubular porous element, and a volatile liquid sorbed on the tubular porous element. The volatile liquid sorbed on the tubular porous element of the canister may by the same or different to the volatile liquids in the blister capsules.

The container for use in an aerosol-generating system may be an aerosol-generating article or form a portion of an aerosol-generating article. The aerosol-generating article may be used in an aerosol-generating device. As used herein, the term "aerosol-generating device" refers to a device that interacts with an aerosol-generating article to generate an aerosol that is directly inhalable into a user's lungs thorough the user's mouth.

The volatile liquid preferably comprises a nicotine-containing material, such as a tobacco-containing material comprising volatile tobacco flavour compounds which are released from the liquid upon heating. Alternatively, or in addition, the liquid may comprise a non-tobacco material. The liquid may include water, solvents, ethanol, plant extracts and natural or artificial flavours. Preferably, the liquid further comprises an aerosol former. Examples of suitable aerosol formers are glycerine and propylene glycol.

In one embodiment, at least one of the blister capsules comprises a source of nicotine. As such, the volatile liquid within at least one of the blister capsules preferably comprises one or more of nicotine, nicotine base, a nicotine salt, or a nicotine derivative.

The nicotine formulation may comprise natural nicotine or synthetic nicotine. The nicotine formulation may comprise nicotine base, a nicotine salt, such as nicotine-HCl, nicotine-bitartrate, or nicotine-tartrate, or a combination thereof.

The nicotine formulation may comprise an electrolyte forming compound. The electrolyte forming compound may be selected from the group consisting of alkali metal hydroxides, alkali metal oxides, alkaline earth metal oxides, sodium hydroxide (NaOH), calcium hydroxide ($Ca(OH)_2$), potassium hydroxide (KOH) and combinations thereof.

The nicotine formulation may comprise other components including, but not limited to, natural flavours, artificial flavours and antioxidants.

The liquid nicotine formulation may comprise pure nicotine, a solution of nicotine in an aqueous or non-aqueous solvent or a liquid tobacco extract.

The liquid nicotine solution may comprise an aqueous solution of nicotine base, a nicotine salt, such as nicotine-HCl, nicotine-bitartrate, or nicotine-tartrate and an electrolyte forming compound.

The nicotine formulation in the or each blister capsule may be advantageously protected from exposure to oxygen (because oxygen cannot generally pass through the blister shell or sealing film), from exposure to light or from exposure to both light and oxygen, so that the risk of degradation of the nicotine formulation is significantly reduced. Therefore, a high level of hygiene can be maintained.

Where the container, or blister capsule, comprises two or more volatile liquids, at least one of the blister capsules preferably comprises a volatile liquid delivery enhancing compound source. As used herein, by "volatile" it is meant the delivery enhancing compound has a vapour pressure of at least about 20 Pa. Unless otherwise stated, all vapour pressures referred to herein are vapour pressures at 25° C. measured in accordance with ASTM E1194-07.

Preferably, the volatile delivery enhancing compound has a vapour pressure of at least about 50 Pa, more preferably at least about 75 Pa, most preferably at least 100 Pa at 25° C.

Preferably, the volatile delivery enhancing compound has a vapour pressure of less than or equal to about 400 Pa, more preferably less than or equal to about 300 Pa, even more preferably less than or equal to about 275 Pa, most preferably less than or equal to about 250 Pa at 25° C.

The volatile delivery enhancing compound may have a vapour pressure of between about 20 Pa and about 400 Pa, more preferably between about 20 Pa and about 300 Pa, even more preferably between about 20 Pa and about 275 Pa, most preferably between about 20 Pa and about 250 Pa at 25° C.

The volatile delivery enhancing compound may have a vapour pressure of between about 50 Pa and about 400 Pa, more preferably between about 50 Pa and about 300 Pa, even more preferably between about 50 Pa and about 275 Pa, most preferably between about 50 Pa and about 250 Pa at 25° C.

The volatile delivery enhancing compound may have a vapour pressure of between about 75 Pa and about 400 Pa, more preferably between about 75 Pa and about 300 Pa, even more preferably between about 75 Pa and about 275 Pa, most preferably between about 75 Pa and about 250 Pa at 25° C.

The volatile delivery enhancing compound may have a vapour pressure of between about 100 Pa and about 400 Pa, more preferably between about 100 Pa and about 300 Pa, even more preferably between about 100 Pa and about 275 Pa, most preferably between about 100 Pa and about 250 Pa at 25° C.

The volatile delivery enhancing compound may comprise a single compound. Alternatively, the volatile delivery enhancing compound may comprise two or more different compounds.

Where the volatile delivery enhancing compound comprises two or more different compounds, the two or more different compounds in combination have a vapour pressure of at least about 20 Pa at 25° C.

The volatile delivery enhancing compound may comprise an aqueous solution of one or more compounds. Alternatively the volatile delivery enhancing compound may comprise a non-aqueous solution of one or more compounds.

The volatile delivery enhancing compound may comprise two or more different volatile compounds. For example, the volatile delivery enhancing compound may comprise a mixture of two or more different volatile liquid compounds.

Alternatively, the volatile delivery enhancing compound may one or more non-volatile compounds and one or more volatile compounds. For example, the volatile delivery enhancing compound may comprise a solution of one or more non-volatile compounds in a volatile solvent or a mixture of one or more non-volatile liquid compounds and one or more volatile liquid compounds.

The delivery enhancing compound preferably comprises an acid or ammonium chloride. Preferably, the delivery enhancing compound comprises an acid. More preferably, the delivery enhancing compound comprises an acid having a vapour pressure of at least about 5 Pa at 20° C. Preferably, where the container or blister capsules comprises a nicotine-containing volatile liquid, the acid has a greater vapour pressure than the nicotine formulation at 20° C.

The delivery enhancing compound may comprise an organic acid or an inorganic acid. Preferably, the delivery enhancing compound comprises an organic acid. More preferably, the delivery enhancing compound comprises a carboxylic acid. Most preferably, the delivery enhancing compound comprises an alpha-keto or 2-oxo acid.

In a preferred embodiment, the delivery enhancing compound comprises an acid selected from the group consisting of 3-methyl-2-oxovaleric acid, pyruvic acid, 2-oxovaleric acid, 4-methyl-2-oxovaleric acid, 3-methyl-2-oxobutanoic acid, 2-oxooctanoic acid and combinations thereof. In a particularly preferred embodiment, the delivery enhancing compound comprises pyruvic acid or lactic acid.

The tubular porous portion is preferably a sorption element with an acid or ammonium chloride sorbed thereon.

As used herein, by "sorbed" it is meant that the volatile liquid is adsorbed on the surface of the sorption element, or absorbed in the sorption element, or both adsorbed on and absorbed in the sorption element.

The sorption element may be formed from any suitable material or combination of materials. For example, the sorption element may comprise one or more of glass, stainless steel, aluminium, polyethylene (PE), polypropylene, polyethylene terephthalate (PET), polybutylene terephthalate (PBT), polytetrafluoroethylene (PTFE), expanded polytetrafluoroethylene (ePTFE), and BAREX®.

The porous sorption element may comprise one or more porous materials selected from the group consisting of porous plastic materials, porous polymer fibres and porous glass fibres. The one or more porous materials may or may not be capillary materials.

Suitable porous fibrous materials include, but are not limited to: cellulose cotton fibres, cellulose acetate fibres and bonded polyolefin fibres, such as a mixture of polypropylene and polyethylene fibres.

Any feature in one aspect of the invention may be applied to other aspects of the invention, in any appropriate combination. In particular, method aspects may be applied to apparatus aspects, and vice versa. Furthermore, any, some and/or all features in one aspect can be applied to any, some and/or all features in any other aspect, in any appropriate combination.

It should also be appreciated that particular combinations of the various features described and defined in any aspects of the invention can be implemented and/or supplied and/or used independently.

The disclosure extends to methods and apparatus substantially as herein described with reference to the accompanying drawings.

The invention will be further described, by way of example only, with reference to the accompanying drawings in which:

FIGS. 1(a) and 1(b) show a plan view and a side view of a blister capsule according to the present invention;

FIGS. 2a) and 2(b) show a plan view and a side view of an alternative blister capsule according to the present invention;

Figure 1A:
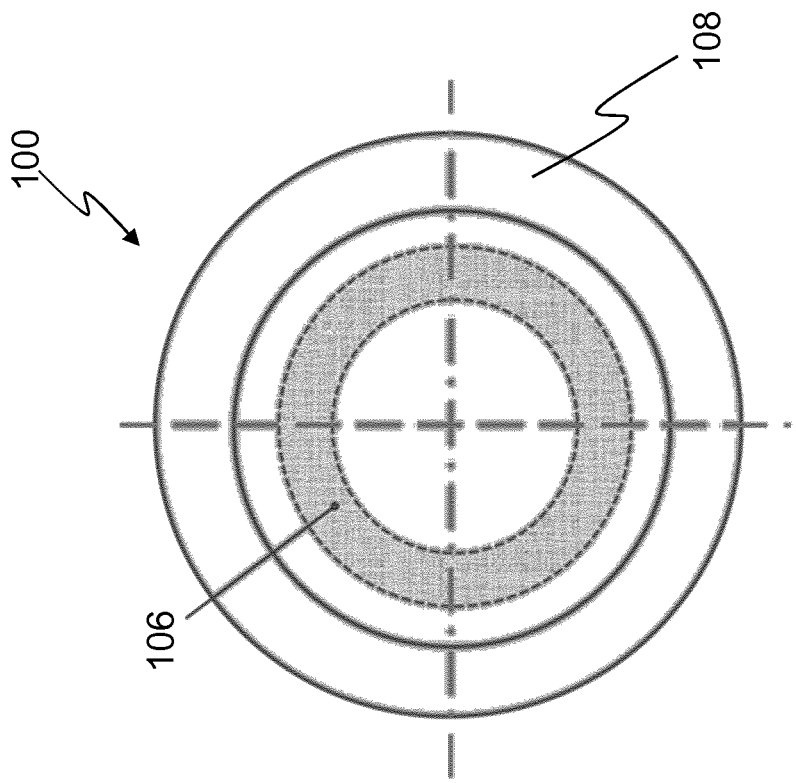
Figure 1B:
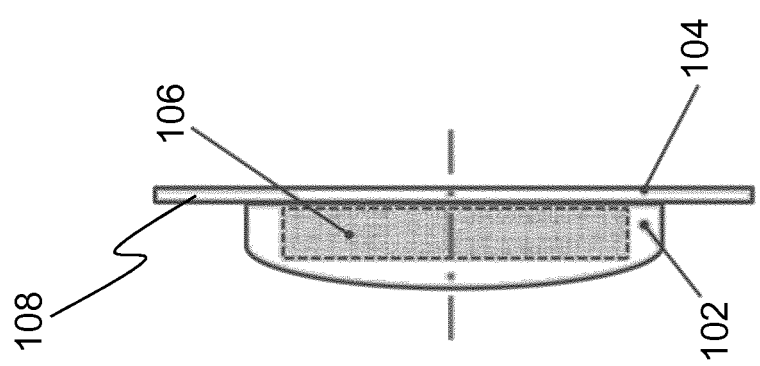

FIGS. 1(a) and 1(b) show a plan view and a side view of a blister capsule 100. The blister capsules comprise a blister shell 102, a sealing film 104, and a tubular porous element 106. The tubular porous element 106 is disposed in a cavity formed by the blister shell 102. The blister shell further comprises a flange 108, provided around the periphery of the cavity. The sealing film 104 is sealed to the flange 108 to form the sealed blister capsule 100. A volatile liquid is sorbed on the tubular porous element 106.

The blister shell 102 and the sealing film 104 are formed from a frangible material. The frangible material is pierceable, for example by an external piercing element. The piercing element may be part of an aerosol-generating device. The materials used to form the blister shell and sealing film are described in further detail below. By forming the blister capsule from frangible materials, the capsule can remain sealed until the point of use.

The volatile liquid can be a nicotine-containing liquid, or a delivery enhancing compound, a flavour compound, or the like.

The blister shell 102 is formed, for example, by punching a blank which is then cold formed using a stamp and mould. The tubular porous element 106 is then provided in the cavity of the blister shell 102, the volatile liquid is provided in the shell, and then the sealing film is sealed to the flange 108. The sealing may be effected by adhesive, heat, or welding, such as ultrasonic welding or laser welding.

Figure 2A:
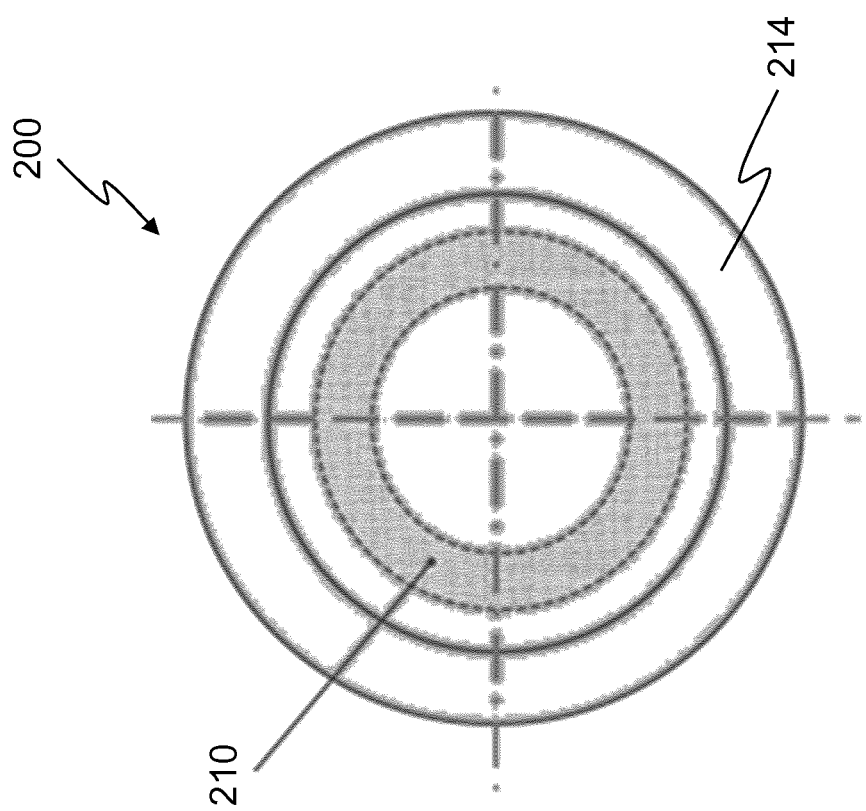
Figure 2B:
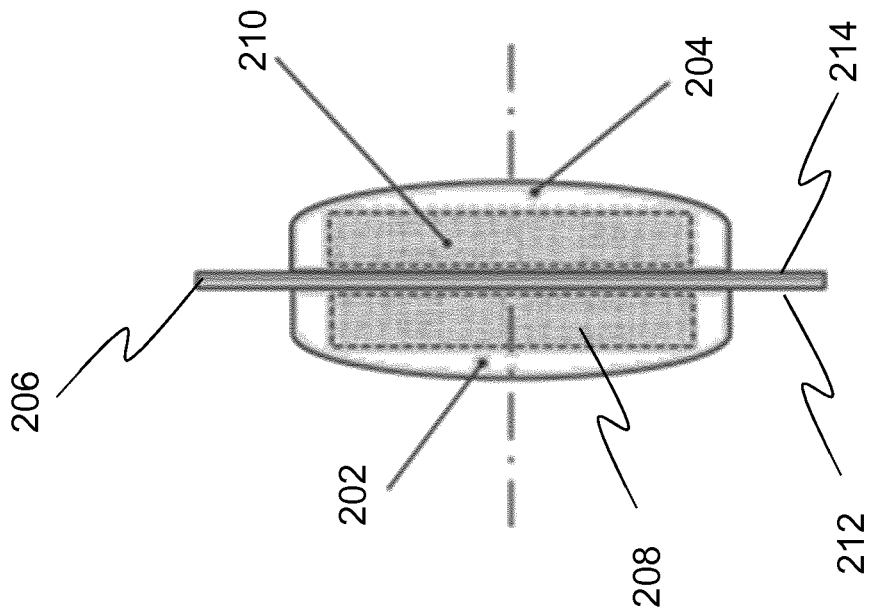

FIGS. 2(*a*) and 2(*b*) show a plan view and a side view of an alternative blister capsule 200. As can be seen, the blister capsule 200 is similar to the blister capsule 100, and comprises a first blister shell 202, a second blister shell 204, a sealing film 206, a first tubular porous portion 208, and a second tubular porous portion 210. The first tubular porous element 208 is disposed in a cavity formed by the first blister shell 202, and the second tubular porous element 210 is disposed in a cavity formed by the second blister shell 204. Each of the first blister shell 202 and the second blister shell 204 comprises a respective flange 212 and 214, provided around the periphery of each cavity. The sealing film 206 is sealed to both flange 212 of the first blister shell 202 and to the flange 214 of the second blister shell 204 to form the sealed blister capsule 200. Volatile liquid is sorbed on both the first tubular porous element 206 and the second tubular porous element 210. The volatile liquid sorbed on the first tubular porous element 206 may be the same or different to the volatile liquid sorbed on the second tubular porous element 210.

The blister capsule 200 is formed in a similar manner to blister capsule 100, except that the sealing film 206 may be sealed to the second blister shell 204 at the same time as the first blister shell, or subsequently.

Figure 3:
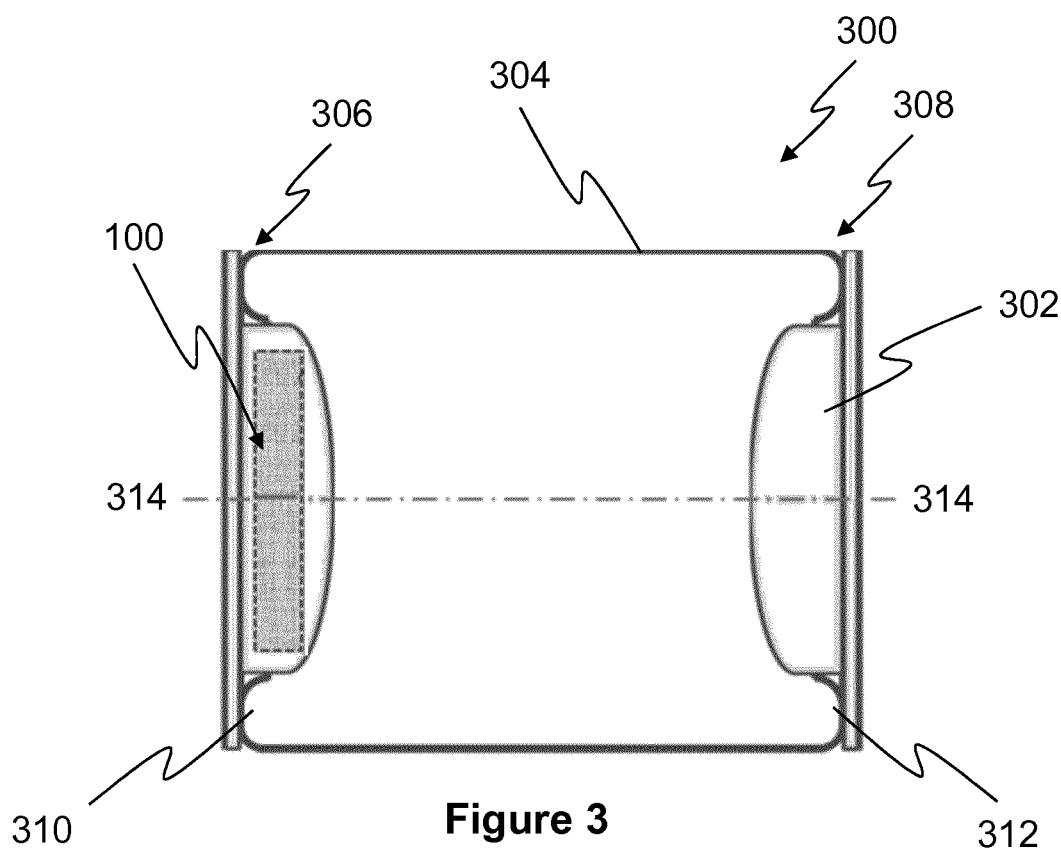
FIG. 3 shows a plan view of a container according to the present invention, incorporating a blister capsule as shown in FIGS. 1(a) and 1(b)

FIG. 3 shows a plan view of a container 300 for use in an aerosol-generating device. The container 300 comprises a blister capsule 100, as described above, a blister capsule 302, and a hollow tubular canister 304. The blister capsule 100 is coupled to the first end 306 of the canister 304, and the blister capsule 302 is coupled to the second end 308 of the canister 304. The first end 306 and second end 308 each comprises an orifice for receiving the respective blister shells of the blister capsules. Each orifice comprises a lip 310 and 312 respectively. The free edge of each lip extends towards the longitudinal axis 314 of the canister 304. Each lip forms a surface which the respective flanges of the blister capsules abut to form a compact and robust canister. The blister capsules may be a press-fit within the orifice of the canister, and may be attached using adhesive, such as an epoxy adhesive, heat sealing, ultrasonic welding, or laser welding.

In use, the hollow tubular canister 304 is a mixing chamber enabling the volatile liquid of the blister capsules to mix and form an aerosol once the capsules have been ruptured by piercing or otherwise. Further details of the use of the container in an aerosol-generating device are provided below.

The canister 304 may be formed using any suitable conventional manufacturing processes. For example, the canister may be formed by extruding a hollow tube, cutting the tube into discrete portions, and then forming the lips 310 and 312 using a necking process or rolling process. In an alternative, the lips are formed separately, for example using a stamp and mould, and then attached to each end of the plane tube. The lip portions may be attached by solder, adhesive, welding, or by a press-fit.

Alternatively, the canister 304 may be formed from a blank, punched from sheet material which is then drawn in a die to form a cup shape having one closed end. The closed end of the drawn cup is then cut out, for example in a further punching process, and then the lips 310 and 312 are formed as described above. In a further alternative, the canister 304 may be formed by cutting a suitably sized sheet of material, and then forming the lips 310 and 312 in a shaped rolling process which also forms the hollow tubular portion of the canister. The side-seam may then be joined by solder, adhesive or by welding.

Figure 4:
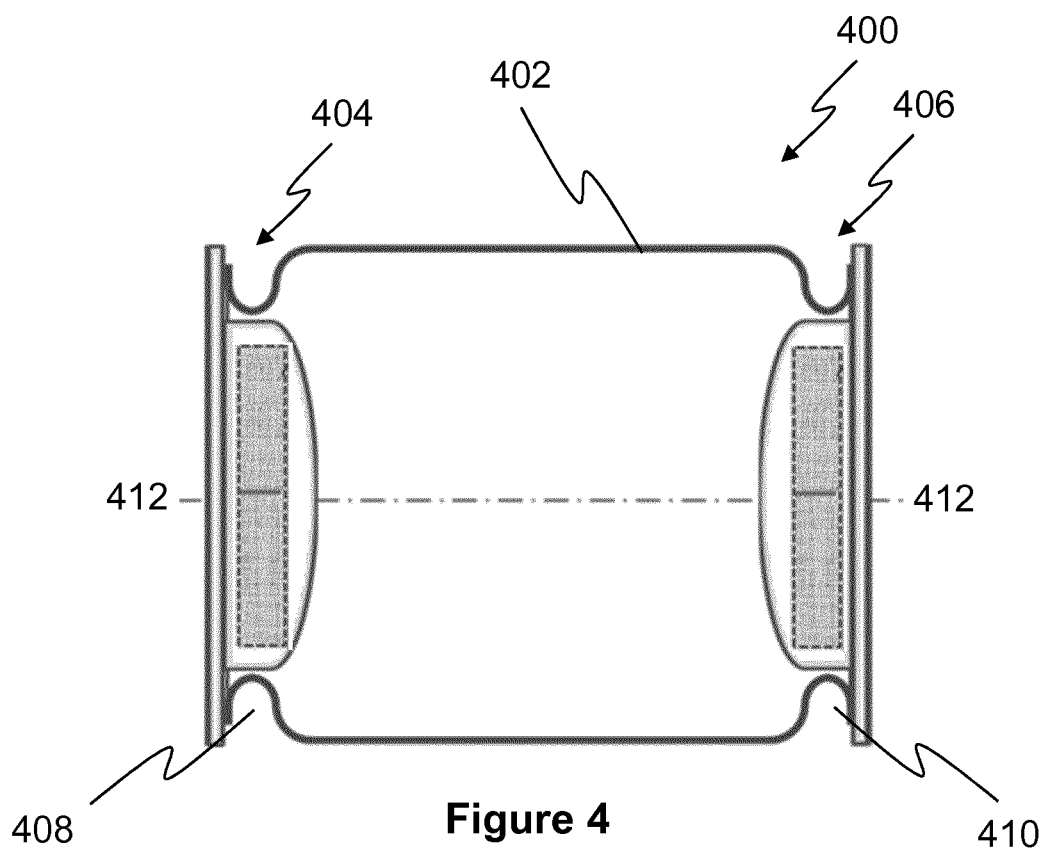
FIG. 4 shows a plan view of an alternative container according to the present invention, incorporating two blister capsules as shown in FIGS. 1(a) and 1(b)

FIG. 4 shows a plan view of an alternative container 400 for use in an aerosol-generating device. The container 400 comprises a first blister capsule 100, a second blister capsule 100, and a hollow tubular canister 402. The blister capsule 100 is coupled to the first end 404 of the canister 402, and the second blister capsule 100 is coupled to the second end 406 of the canister 402. The first end 404 and second end 406 each comprises an orifice for receiving the respective blister shells of the blister capsules. Each orifice comprises a lip 408 and 410 respectively. The free edge of each lip extends away from the longitudinal axis 412 of the canister 402. Each lip forms a surface which the respective flanges of the blister capsules abut to form a compact and robust canister.

The canister 402 may be formed in a similar manner to that of canister 304 described above.

Figure 5:
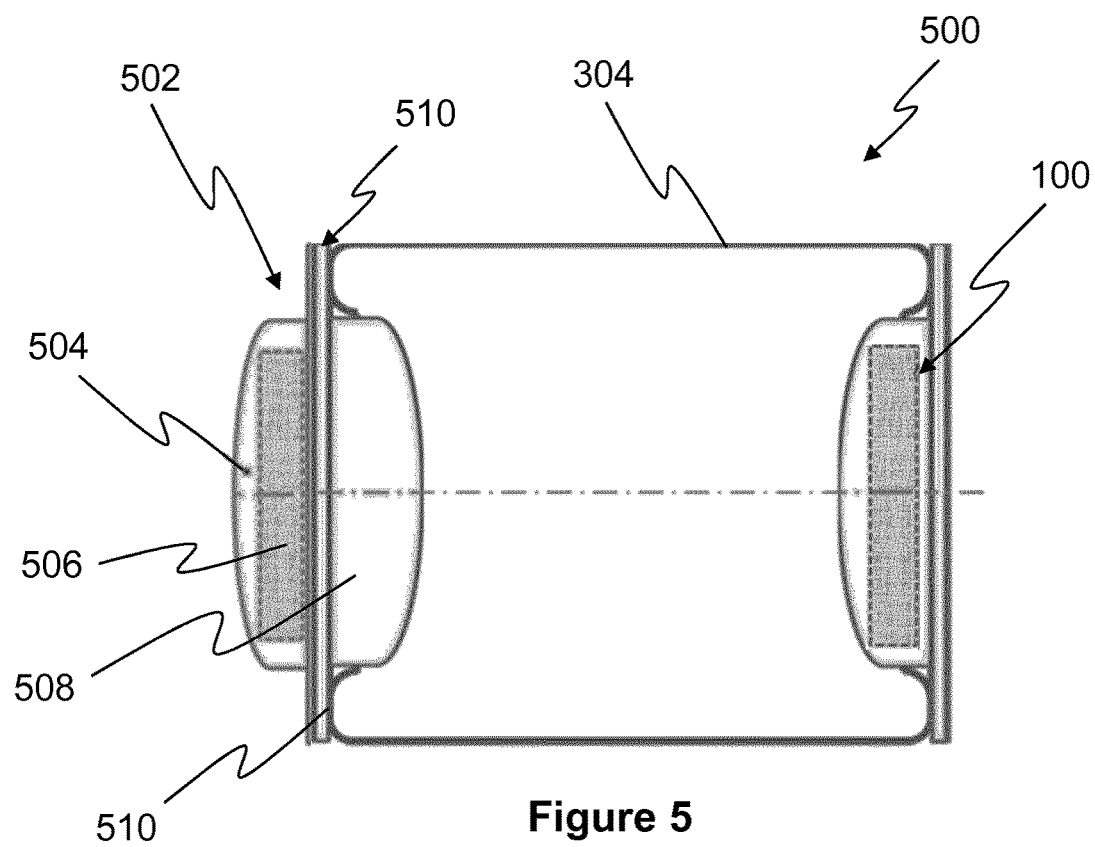
FIG. 5 shows a plan view of a yet further alternative container according to the present invention, incorporating blister capsules.

FIG. 5 shows a plan view of a further alternative container 500. The container 500 is similar to the container 300 shown in FIG. 3, and described above, and comprises the same hollow tubular canister 304. The container 500 further comprises a blister capsule 502 and a blister capsule 100. The blister capsule 502 comprises a first blister shell 504 having a tubular porous element 506 for sorbing a volatile liquid, and a second blister shell 508 for containing a further liquid or solid aerosol-generating substrate. A sealing film 510 is provided between the first blister shell 504 and the second blister shell 508 for sealing both blister shells. The blister shells are coupled to the canister 304 in the same way as described above with reference to FIG. 3. The liquids contained within each blister capsule may be the same or different.

Figure 6:
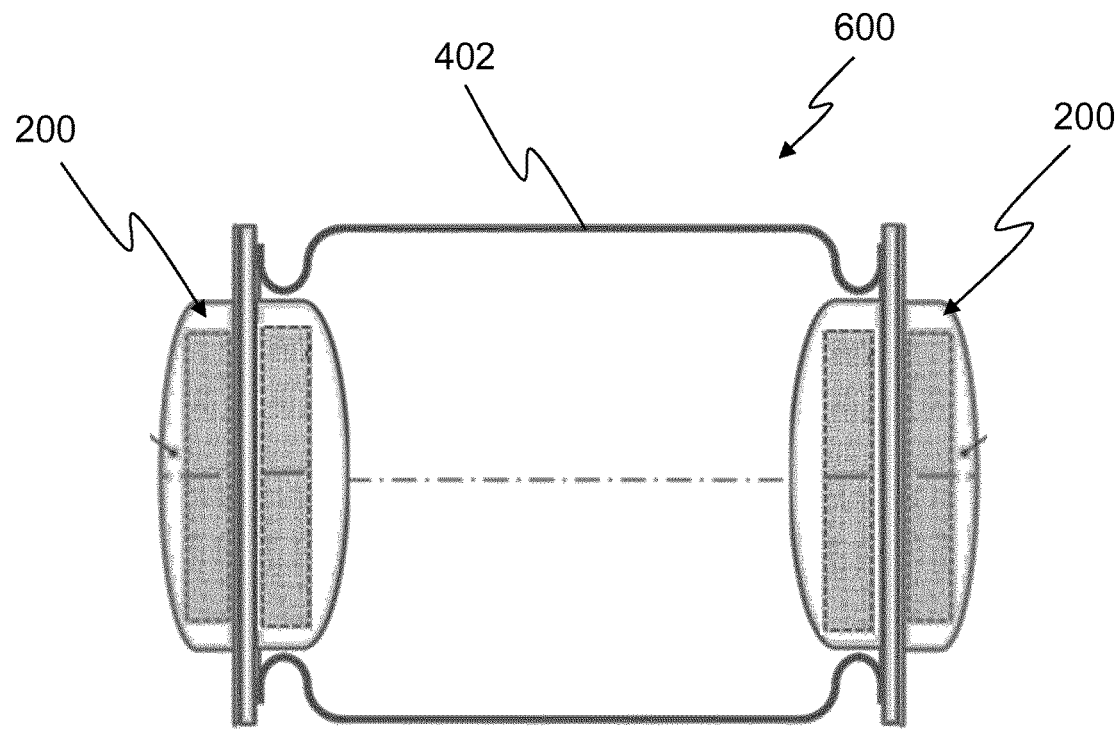
FIG. 6 shows a plan view of a still further alternative container according to the present invention, incorporating two blister capsules as shown in FIGS. 2(a) and 2(b)

FIG. 6 shows a plan view of a still further alternative container 600. The container 600 is similar to the container 400 shown in FIG. 4, and described above, and comprises the same hollow tubular canister 402. The container 600 further comprises two blister capsules 200 each coupled to an end of the canister 402. The liquids contained within each blister capsule may be the same or different. In this example shown in FIG. 6, the liquids may be a nicotine-containing volatile liquid, a volatile delivery enhancing compound, such as pyruvic acid or lactic acid, a volatile liquid flavour compound, such as menthol, and a further volatile liquid flavour compound, such as clove.

As will now be appreciated, any combination of the blister capsules and canisters described herein may be provided. In this way, containers may be provided to suit the particular requirement. For example, containing three blister capsules, containing a nicotine-containing liquid, a liquid delivery enhancing compound and a liquid flavour compound respectively.

The sealing films, blister shells, and canisters described above are formed from a laminate material.

Figure 7:
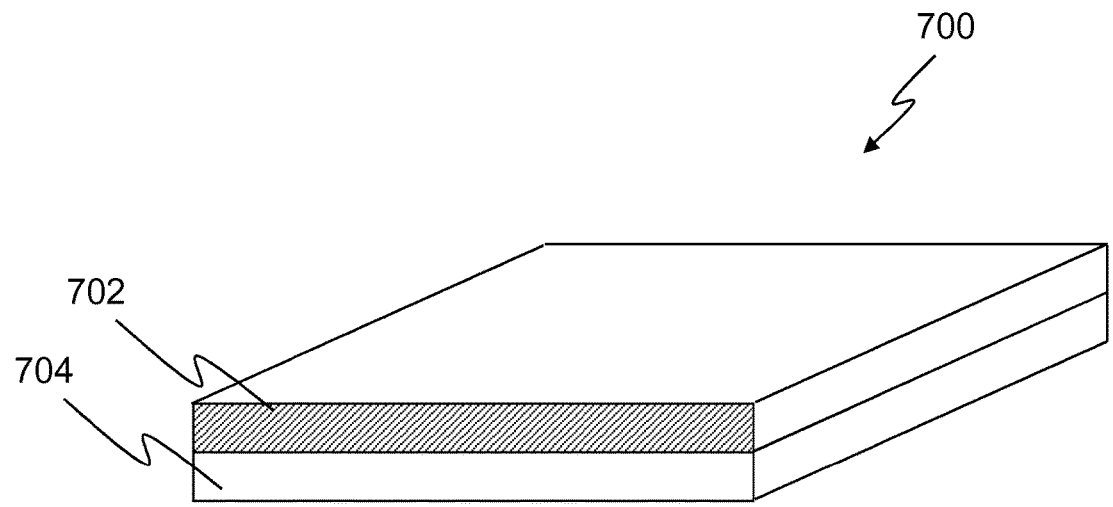
FIG. 7 shows a laminate material used in the blister capsules according to the present invention.

FIG. 7 shows such a laminate material 700 comprising two layers of material. The first layer 702 is of aluminium foil, and the second layer 704 is of a polymer material. The aluminium foil layer 702 forms the external surface of the sealing film, and the polymer layer 704 forms the internal layer which comes into contact with the volatile liquid.

Figure 8:
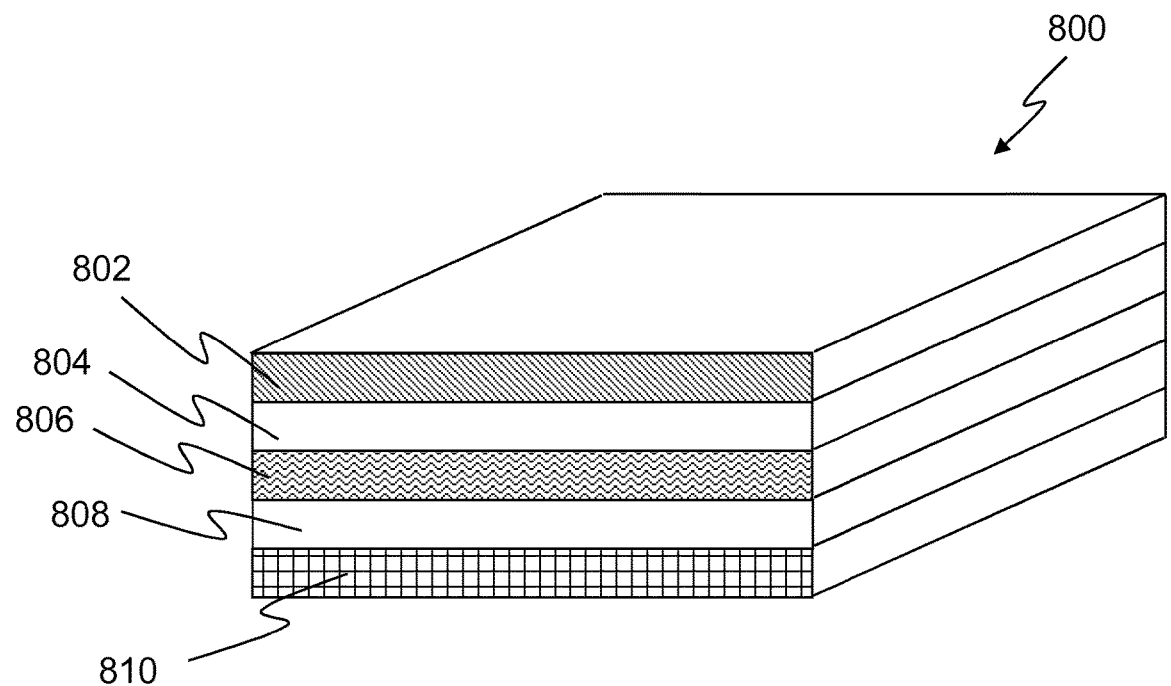
FIG. 8 shows an alternative laminate material used in the blister capsules according to the present invention.

FIG. 8 shows a further example of such a laminate material 800 comprising three layers of material, and two layers of adhesive. The laminate material 800 comprises a layer 702 of a polymer material, a first layer of adhesive 804, a layer 806 of aluminium foil, a second layer of adhesive 808 and a layer of a second polymer material 810.

The polymer material for the laminates may be polypropylene, polyurethane, polyethylene, fluorinated ethylene propylene, or any other suitable polymer.

The laminate 700 is particularly useful when forming a blister capsule 100 as shown in FIGS. 1(*a*) and 1(*b*) above, when only a single side of the sealing film is used to seal a blister shell. The material for the external polymer layer 704 can be chosen in dependence on the volatile liquid that it will come into contact with.

The laminate 800 is particularly useful when forming a blister capsule 200 as shown in FIGS. 2(*a*) and 2(*b*) above, when two different volatile liquids are provided. The material for the external polymer layers 802 and 810 can be chosen in dependence on the volatile liquid that it will come into contact with. This can ensure that the polymer layer does not degrade, and forms a suitable seal to maintain the liquid in the blister shell during storage.

The above described containers may be used in an aerosol-generating device comprising a cavity configured to receive the container, a piercing element configured to pierce the frangible blister shells and sealing films, at least one air inlet, and at least one air outlet.

In one example, the container comprises a volatile nicotine-containing liquid in one blister capsule and a volatile delivery enhancing compound liquid in another blister capsule. In use, as the container is inserted into the cavity of the aerosol generating device the piercing element is inserted into the container and pierces the shells and frangible sealing films. This allows a user to draw air into the container through the air inlets, downstream through the tubular porous element, through the hollow tubular canister, through the other of the blister capsule and tubular porous element at the other end of the container and out through the air outlets.

Volatile delivery enhancing compound vapour is released from the volatile delivery enhancing compound source in the tubular porous portion into the air stream drawn through the device and nicotine vapour is released from the nicotine source into the air stream drawn through the device. The volatile delivery enhancing compound vapour reacts with the nicotine vapour in the gas phase in the mixing chamber to form an aerosol, which is delivered to the user through the air outlets.

As will be appreciated, the capsules and containers of the present invention may be used with any other suitable type of aerosol-generating device. For example, a device having and electrically operated heater may be suitable, the heater configured to aerosolise the volatile liquid to be inhaled by the user.

The invention claimed is:

1. A blister capsule for an aerosol-generating system, comprising:
    a blister shell, wherein a depth of the blister shell is less than a diameter of the blister shell;
    a tubular porous element disposed in the blister shell;
    a volatile liquid sorbed on the tubular porous element;
    a further blister shell;
    a further tubular porous element disposed in the further blister shell;
    a further volatile liquid sorbed on the further tubular porous element; and
    a film configured to seal the blister shell and the further blister shell,
    wherein the film is positioned between the blister shell and the further blister shell so that the blister shell is positioned on a first side of the film and the further blister shell is positioned on a second side of the film, and
    wherein the film and the blister shell are frangible.

2. The blister capsule according to claim 1, wherein the blister shell comprises a cavity and a flange extending around a periphery of the cavity, the tubular porous element being disposed in the cavity of the blister shell.

3. The blister capsule according to claim 2, wherein the film is sealed to the flange.

4. The blister capsule according to claim 1, wherein the volatile liquid is different from the further volatile liquid.

5. The blister capsule according to claim 1, the capsule having a substantially circular cross-section.

6. The blister capsule according to claim 1, wherein the blister shell is formed from a laminate material comprising at least two layers.

7. The blister capsule according to claim 1, wherein the volatile liquid comprises one or more of nicotine, nicotine base, a nicotine salt, or a nicotine derivative.

* * * * *